US011903771B2

(12) United States Patent
Meral et al.

(10) Patent No.: US 11,903,771 B2
(45) Date of Patent: Feb. 20, 2024

(54) AUTOMATED TUMOR IDENTIFICATION DURING SURGERY USING MACHINE-LEARNING

(71) Applicant: KONINKLIJKE PHILIPS N.V., Eindhoven (NL)

(72) Inventors: Faik Can Meral, Mansfield, MA (US); Shyam Bharat, Arlington, MA (US); Ramon Quido Erkamp, Swampscott, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 225 days.

(21) Appl. No.: 17/055,716

(22) PCT Filed: May 1, 2019

(86) PCT No.: PCT/EP2019/061164
§ 371 (c)(1),
(2) Date: Nov. 16, 2020

(87) PCT Pub. No.: WO2019/219387
PCT Pub. Date: Nov. 21, 2019

(65) Prior Publication Data
US 2021/0204914 A1 Jul. 8, 2021

Related U.S. Application Data

(60) Provisional application No. 62/672,108, filed on May 16, 2018.

(51) Int. Cl.
*A61B 8/00* (2006.01)
*A61B 8/08* (2006.01)
(Continued)

(52) U.S. Cl.
CPC ............... *A61B 8/54* (2013.01); *A61B 8/085* (2013.01); *A61B 8/0808* (2013.01);
(Continued)

(58) Field of Classification Search
CPC ......... A61B 8/54; A61B 8/0808; A61B 8/085; A61B 8/0891; A61B 8/463; A61B 8/469;
(Continued)

(56) References Cited

U.S. PATENT DOCUMENTS

2005/0101855 A1   5/2005  Miga et al.
2010/0322489 A1*  12/2010 Tizhoosh ............... G06T 7/174
                                                          345/157
(Continued)

FOREIGN PATENT DOCUMENTS

CN    104851101 A    8/2015
JP    H06233761 A    8/1994
WO    2018015414 A1  1/2018

OTHER PUBLICATIONS

Azizi et al: "Toward a Real-Time System for Temporal Enhanced Ultrasound-Guided Prostate Biopsy"; International Journal of Computer Assisted Radiology and Surgery (2018), 13:1201-1209.
(Continued)

*Primary Examiner* — Baisakhi Roy
*Assistant Examiner* — Kaitlyn E Sebastian (57) ABSTRACT

An ultrasound (US) system (10) includes a US scanner (14) and a US probe (12) operatively connected to the US scanner. At least one electronic processor (20) is programmed to: control the US scanner and US probe to acquire a series of preoperative images of a tumor and surrounding blood vessels in a region of interest (ROI) of a patient; provide a graphical user interface (GUI) (26) via which the acquired preoperative images are labeled with contours of the tumor and the surrounding blood vessels in the ROI; tune
(Continued)

a trained neural network (30) for the patient using the labeled preoperative images to generate a patient-tuned trained neural network; perform live imaging by controlling the US scanner and US probe to acquire live images of the tumor and the surrounding blood vessels in the ROI of the patient; input the live images to the patient-tuned trained NN to output live contours of the tumor and the surrounding blood vessels; and control a display device (24) to display the live images with the live contours superimposed.

18 Claims, 4 Drawing Sheets

(51) Int. Cl.
    *G16H 30/40*     (2018.01)
    *G16H 40/63*     (2018.01)
    *G06N 3/08*     (2023.01)
    *G06N 3/04*     (2023.01)
    *G06N 3/044*     (2023.01)

(52) U.S. Cl.
    CPC ............ *A61B 8/0891* (2013.01); *A61B 8/463* (2013.01); *A61B 8/469* (2013.01); *A61B 8/5261* (2013.01); *G06N 3/044* (2023.01); *G06N 3/08* (2013.01); *G16H 30/40* (2018.01); *G16H 40/63* (2018.01)

(58) Field of Classification Search
CPC ..... A61B 8/5261; A61B 8/4245; A61B 8/483; A61B 8/468; A61B 2090/364; A61B 2090/378; A61B 5/0035; A61B 5/055; G06N 3/0445; G06N 3/08; G06N 3/0454; G06N 3/084; G16H 30/40; G16H 40/63; G06T 2207/10088; G06T 2207/10132; G06T 2207/20081; G06T 2207/20084; G06T 2207/20104; G06T 2207/30096; G06T 2207/30101; G06T 7/0014; G06T 7/11

See application file for complete search history.

(56) References Cited

U.S. PATENT DOCUMENTS

| | | | |
|---|---|---|---|
| 2016/0035093 A1* | 2/2016 | Kateb | ............... G02B 21/0012 382/131 |
| 2016/0217560 A1 | 7/2016 | Tahmasebi et al. | |
| 2018/0015414 A1 | 1/2018 | Hu et al. | |
| 2018/0144466 A1* | 5/2018 | Hsieh | ................... G06T 7/0012 |
| 2019/0287246 A1* | 9/2019 | Pfister | ................. G06V 20/698 |
| 2019/0388160 A1 | 12/2019 | Wood et al. | |

OTHER PUBLICATIONS

Comeau eta l: "Intraoperative US in Interactive Image-Guided Neurosurgery"; Imaging & Therapeutic Technology, Radiographics 1998, vol. 18, pp. 1019-1027.

Mercier et al: "New Prototype Neuronavigation System Based on Preoperative Imaging and Intraoperative Freehand Ultrasound: System Description and Validation"; Int J Cars (2011) 6:507-522.

* cited by examiner

AUTOMATED TUMOR IDENTIFICATION DURING SURGERY USING MACHINE-LEARNING

CROSS-REFERENCE TO PRIOR APPLICATIONS

This application is the U.S. National Phase application under 35 U.S.C. § 371 of International Application No. PCT/EP2019/061164, filed on May 1, 2019, which claims the benefit of U.S. Provisional Patent Application No. 62/672,108, filed on May 16, 2018. These applications are hereby incorporated by reference herein.

FIELD

The following relates generally to image guided interventional procedures, image guided neurosurgery, image guided brain surgery, ultrasound imaging arts, ultrasound probe tracking arts, ultrasound image displaying, and related arts.

BACKGROUND

Pre-operative Magnetic Resonance Imaging (MRI) in neurosurgery is a usual standard used for identifying the pathology and planning the surgery prior to surgical resection of tumors. One or more tumors and surrounding vasculature are segmented on the pre-operative MR images and used in pre-operative planning Neuro-navigation is used during neurosurgery to enable surgeons to navigate their way through the craniotomy to the pathology. High accuracy tracking technologies, such as optical tracking is used to track surgical tools for neuro-navigation. The tracking information is registered to the patient and preoperative images such that surgeons can navigate in the skull and perform the surgery as planned based on the pre-operative imaging. However several factors make the brain deform during the surgery and diminish the utility of pre-operative imaging for neuro-navigation. This phenomenon, which is called brain shift, is well known in the neurosurgery practice and usually the brain shift starts with the craniotomy and becomes more pronounced after subsequent removal of the dura (the thick fibrous membrane which holds the brain tissue in place). Other factors that can cause brain shift include swelling, gravity, tumor resection, and cerebrospinal fluid drainage. Generally speaking, brain shift always gets worse throughout the procedure.

Intraoperative or "live" imaging can reveal the brain shift and guide the surgeon to make modifications to the surgical plan or update it. Among available modalities, MRI provides unsurpassed image quality and resolution. However it is disruptive to the surgical workflow (no ferrous metals can be found in the room, other metals cannot be placed close to the imaging area, therefore extensive patient preparation is necessary for each intraoperative MRI image acquisition), time consuming (MR sequences take up to 45 min), and unavailable except in high end surgical suites. On the other hand intraoperative ultrasound (US) is not as disruptive as MRI (no limitations as to metals, and no extensive patient preparation), can be performed in minutes with real time image visualization, and is widely available. However image quality and resolution of US is poor compared to MRI, registration of US to MRI is not a straightforward task, and not all tumors are visible in US imaging.

To accommodate these difficulties when using intraoperative ultrasound, initial (preoperative) ultrasound images are acquired after craniotomy but before removing the dura. With the dura still in place, the brain shift is minimal and the preoperative US image registers well with the preoperative MRI. Such image registration provides surgeons with a visual understanding of how the tumor looks under ultrasound when viewed together with the overlaid segmentation of the tumor. After removing the dura the rigid registration of ultrasound to preoperative MR images is not usually sufficiently accurate for intraoperative navigation. At this point, segmentation can still be presented overlaid on top of intraoperative ultrasound images to help interpret the intraoperative (i.e. live) images, though the alignment of the segmentation with the live images may not be very accurate due to the sub-optimal registration.

After brain shift, the preoperative MRI tumor segmentation and overlay on the US image becomes invalid, because the US image displays tissue after deformation while segmentation is still for the un-deformed tissue. At this point the experience of the surgeon, in US and MRI image interpretation and the understanding of how the particular tumor was located within the anatomy and how it would deform, is the distinguishing factor and assists the surgeon to decide what is residual tumor and what is not based on the intra-operative US images of the deformed brain tissue.

Various non-rigid registration techniques have been used by researchers to address the problem of usability of intra-operative US for brain surgery in the presence of brain shift, however with limited success. In a first example technique, the pre-operative MR image is deformed based on the intra-operative ultrasound image, although this approach can introduce substantial inaccuracy because in most cases two-dimensional (2D) ultrasound images corresponding to a plane is used, which do not capture any deformations in the out of plane direction. In a second example technique, an optical surface scan of the deformed brain tissue is performed to compute the volumetric deformation of the brain through finite element modeling. This approach is limited to visualization of lesions close to the surface of the brain and does not provide accurate information about the deeper lesions.

The following discloses new and improved systems and methods to overcome these problems.

SUMMARY

In one disclosed aspect, an US system includes a US scanner and a US probe operatively connected to the US scanner. At least one electronic processor is programmed to: control the US scanner and US probe to acquire a series of preoperative images of a tumor and surrounding blood vessels in a region of interest (ROI) of a patient; provide a graphical user interface (GUI) via which the acquired preoperative images are labeled with contours of the tumor and the surrounding blood vessels in the ROI; tune a trained neural network for the patient using the labeled preoperative images to generate a patient-tuned trained neural network; perform live imaging by controlling the US scanner and US probe to acquire live images of the tumor and the surrounding blood vessels in the ROI of the patient; input the live images to the patient-tuned trained NN to output live contours of the tumor and the surrounding blood vessels; and control a display device to display the live images with the live contours superimposed.

In another disclosed aspect, a non-transitory storage medium stores instructions readable and executable by a processor in operative communication with an US system and a display device to perform a live brain imaging method. The method includes: controlling the US system to acquire two-dimensional (2D) live brain images; applying a neural network to the 2D live brain images to generate live contours of a tumor and surrounding blood vessels imaged in the 2D live brain images; and controlling the display device to present the 2D live brain images with the live contours superimposed.

In another disclosed aspect, an US system includes a US scanner and a US probe operatively connected to the US scanner. At least one electronic processor is programmed to: control the US scanner and the US probe to acquire 2D live images of a ROI; apply a neural network to the 2D live brain images to generate live contours of a tumor and surrounding blood vessels imaged in the 2D live images; and control a display device to present the 2D live images with the live contours superimposed.

One advantage resides in determining tumor positions during brain shift.

Another advantage resides in utilizing machine learning to train a neural network to learn correlations between pre-operative tumor contours and intra-operative tumor contours during brain shift.

Another advantage resides in predicting a new position of a tumor due to brain shift during a surgical procedure.

Another advantage resides in providing an overlay of MR images and US images having tumor contours changed due to brain shift.

Another advantage resides in providing one or more of the foregoing advantages employing only ultrasound imaging without the need for MR imaging after acquisition of the initial preoperative MR images, and without the need for update contouring of the tumor or blood vessels during the neurosurgery.

Another advantage resides in providing one or more of the foregoing advantages in which additional information in the form of intraoperative MR images, if available, can be used to improve the contour estimation in the intraoperative US images.

Another advantage resides in providing one or more of the foregoing advantages in which additional information in the form of manual contouring of intraoperative MR images, if available, can be used to improve the contour estimation in subsequent intraoperative US images.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

In image-guided brain surgery, ultrasound (US) is commonly used to provide intraoperative imaging during the surgical procedure. In a typical workflow, a pre-operative MRI image is acquired and the tumor and critical blood vessels are segmented and the surgery is planned. On the day of surgery, the patient is prepared and a portion of the skull removed (i.e., a craniotomy) to provide access to the outermost dura membrane enveloping the brain. At this point a pre-operative US image is acquired and displayed. The US imaging is tracked using cameras or other positioning sensors, and the tumor/blood vessels contours manually drawn in the pre-operative MRI image are superimposed on the display of the pre-operative US image, possibly after a rigid spatial registration of the preoperative MRI and US images. Alternatively, the US imaging probe can be a 2D matrix array probe creating three-dimensional (3D) images of a volume. In this case MRI based segmentation can be superimposed as contours on the 2D slices of the 3D volume image, or as a volume (possibly with different color coding and transparency) on the 3D US volume itself. The 2D matrix array probe can be tracked to obtain smoother images by spatial averaging. The visual appearance of the tumor may be quite different in the US modality versus MRI, and the surgeon visually inspects the pre-operative US image to identify the target tumor(s) for removal. Then, a portion of the dura is removed to provide access to the brain and surgical tumor removal commences. Live US images (i.e. intraoperative) acquired intermittently throughout the procedure are visualized with the tumor/blood vessels contours from the MRI image superimposed on the live US images as a reference.

A problem arises, however, with brain shift, in that the brain can deform during the surgery, e.g. as the dura is removed and as tumor tissue is removed causing the tumor size to shrink over the course of the surgery. Brain shift can result in the superimposed contours from the MRI no longer accurately reflecting the positions of the corresponding anatomy as shown in the live US imaging. Conventionally, this is addressed by the surgeon visually detecting the shift in the live US images (and based on other feedback, e.g. tactile feedback) and mentally accounting for the shift. If an intra-operative MRI scanner is available in the surgical suite then updated MRI images may be occasionally acquired and segmented to produce updated MRI contours. However, the MRI is generally not capable of providing real-time live imaging. It should be noted that the surgical removal of the brain tumor can take several hours, and that precision on the order of microns is sometimes required. Brain shift can occur gradually over the course of the surgery, e.g. as more tumor tissue is removed this can change pressure on surrounding brain tissue leading to progressively greater brain shift, such that an occasional intra-operative MRI is not sufficient for guidance throughout the procedure.

In approaches disclosed herein, a trained neural network to generate an up-to-date contour of the tumor and major blood vessels directly from the intraoperative US images is described. This allows for tracking of brain shift as it may change gradually over the course of the surgical procedure. In some embodiments, the contours from the MRI continue to be superimposed, and these newly generated up-to-date contours from the neural network are also superimposed, e.g. using different color coding, to provide maximal information to the surgeon.

Training of the neural network must be very precise, and must furthermore accommodate patient-specific variations. To this end, the disclosed approach employs initial training of the neural network using historical patient data, and patient-specific fine tuning comprising update training of the neural network using the initial pre-operative US image labeled with the contours from the pre-operative MRI or with corresponding contours adjusted or newly drawn by the neurosurgeon in the preoperative US images.

During surgery, the input data to the neural network is a sequence of 2D ultrasound images (that is, the intraoperative or "live" US images used to provide visual guidance to the surgeon during the surgery), or one or a sequence of 3D ultrasound images which can be sliced and for processing through the neural network, alternatively a network can be trained to work with 3D US volumetric images as input. The output of the neural network is one or more tumor and/or blood vessel contours.

For the initial training, appropriate training data can be collected from past similar brain surgeries, using pre-operative US images which are labeled with the corresponding MRI-derived tumor and blood vessel contours serving as ground-truth contours. Since the pre-operative US images are acquired after the craniotomy but prior to cutting into the dura and prior to removal of any tumor tissue, brain shift should be negligible in the training data. Conventional backpropagation training may be used to train the neural network to output contours that optimally match the ground truth contours manually drawn in the pre-operative MRI images.

The fine tuning employs as training data the pre-operative image of the current patient labeled with the MRI contours, again serving as ground truth. (More precisely, this training data consists of a set of pre-operative 2D US image slices that may be combined to provide a 3D pre-operative US image, or a 3D US volumetric image obtained using a 2D matrix array probe for 3D imaging, labeled with the MRI contours and/or with contours which are adjusted or newly drawn in the preoperative US images by the neurosurgeon). The same backpropagation-based training that was used in the initial training of the neural network may be employed in the update training in order to provide the fine tuning, and the resulting fine-tuned neural network is specific to the current patient.

If an MRI scanner is available in the surgical suite, then it is contemplated to perform additional fine tuning steps at various points during the surgical procedure. For example, after several hours and removal of a substantial portion of the brain tumor, the fine-tuned neural network may be out of date (i.e. lacks the prediction accuracy needed for surgery), and a new MRI image may be acquired and manually contoured, along with a corresponding current US image. This then serves as update training data for further fine tuning (i.e. update training) of the neural network.

In some embodiments, the neural network may be a recurrent neural network (RNN) in which the contours output for a current US image depend on the previous contours output for previous US images in the sequence. This reflects the expectation that (1) the tumor will decrease in size over the course of the surgery due to tumor tissue removal, and (2) this shrinkage will be gradual. However, in order to train the RNN it is necessary to have labeled sequence training data over the course of the surgery, which could be provided in cases in which there is an MRI scanner in the surgical suite to provide occasional updated MRI (i.e. ground truth) contour labeling.

In yet a further variant, it is contemplated to employ reinforcement learning (RI) in which occasionally an US image of the live sequence is manually contoured, and the fidelity of this manual US contour to the contour output by the trained and fine-tuned neural network is used as further feedback for update training (i.e. RI) of the neural network. In some examples, the RI can executed using the MRI driven contours rather than manual contours. Any errors made by the neural network during prediction can be accounted for due the RI, and so the neural network can be more conservative for that specific type of error.

In general, the neural network is configured to receive as input a sequence of 2D US images (which may, or may not, collectively make up a 3D image) and to output one or more contours in the spatial reference of the US image plane. Any neural network architecture may be used in the embodiments disclosed herein.

In illustrative embodiments, the disclosed approach is used in brain surgery procedures employing pre-operative MRI imaging and intraoperative US imaging. Brain imaging for neurosurgery guidance calls for high precision as compared with many other interventional procedures in which organ shift or deformation can be sufficiently accommodated by mental correction or elastic registration techniques. However, more generally the disclosed approaches may find application in other types of interventional procedures such as prostate, breast, or liver biopsy procedures in which organ deformation may occur and is beneficially tracked over the course of a surgical procedure.

Figure 1:
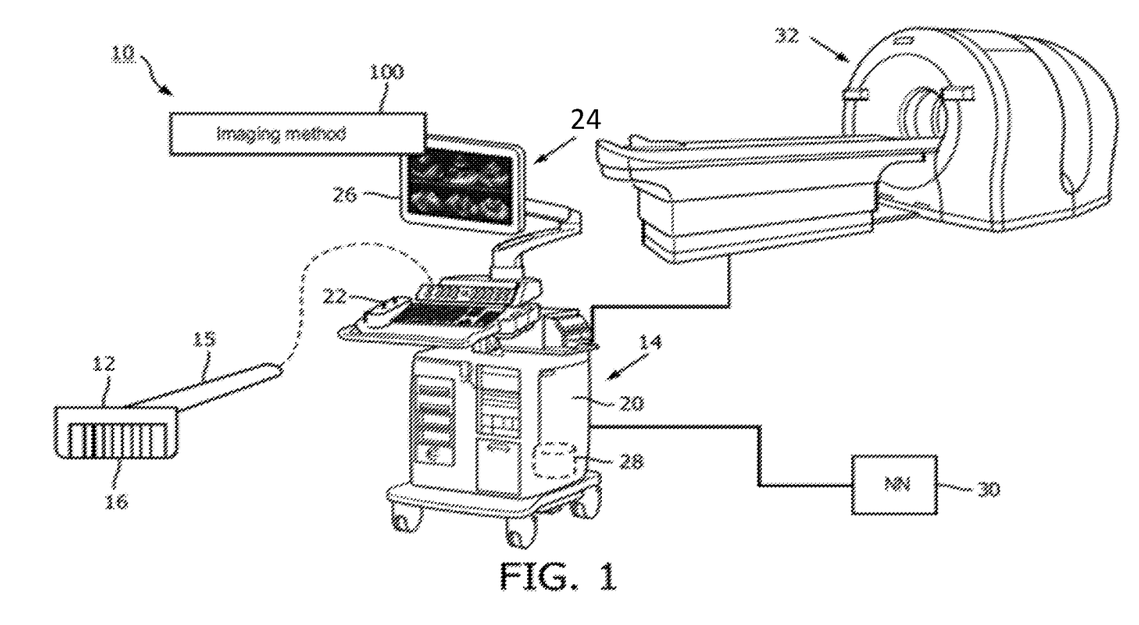
FIG. 1 diagrammatically shows an illustrative ultrasound (US) image guidance device for use in neurosurgery in accordance with one aspect.

With reference to FIG. 1, an illustrative interventional imaging device suitable for implementing the foregoing is shown. An ultrasound (US) imaging device 10 may, for example, be an EPIQ™ ultrasound imaging system available from Koninklijke Philips N.V., Amsterdam, the Netherlands, a UroNav™ system for US/MRI-fusion-guided prostate biopsy available from Koninklijke Philips N.V., Amsterdam, the Netherlands, the PercuNav™ system (available from Koninklijke Philips N.V., Amsterdam) for general fusion of US with prior 3D imaging (CT, MR, cone-beam CT, etc.), or may be another commercial or custom-built ultrasound imaging system. The ultrasound imaging device 10 includes an US probe 12 operatively connected to an US scanner 14 to perform ultrasound imaging. The illustrative ultrasound probe 12 is connected with the ultrasound imaging system 10 via cabling 15, though a wireless connection is contemplated. The US probe 12 includes a sensor array 16 that acquires a two-dimensional (2D) image frame in a sonicated plane. The surgeon or other operator can adjust the location and orientation (i.e. "pose") of the image frame by free-hand or supported movement of the ultrasound probe 12. Such free-hand motion may entail a translational sweep of the US probe 12 (and hence of the sonicated plane) and/or may include rotating the US probe 12 about an axis. The US scanner 14 and the US probe 12 are configured to acquire a "live" succession of two-dimensional or three-dimensional (2D/3D) image frames of a portion of a patient, where each 2D image frame corresponds to the current pose of the sonicated plane, or in the case of 3D imaging, multiple planes can be considered.

The US scanner 14 also includes and/or is operatively connected with at least one electronic processor 20 (e.g., a microprocessor, a microcontroller, and the like), at least one user input device (e.g., a mouse, a keyboard, a trackball, and/or the like) 22, and a display device 24 for displaying ultrasound images and/or US scanner settings, image parameters, and/or so forth. The display device 24 is configured to display a graphical user interface (GUI) 26 including one or more fields to receive a user input from the user input device 22.

The at least one electronic processor 20 is operatively connected with a non-transitory storage medium 28 that stores instructions which are readable and executable by the at least one electronic processor 20 to perform disclosed operations including, e.g. operating the US scanner 14 to acquire preoperative US images and to perform live US imaging and to perform an imaging method or process 100 to obtain images of a patient for neurosurgery guidance. The non-transitory storage medium may, for example, comprise a hard disk drive or other magnetic storage medium; a solid state drive (SSD), flash drive, electronically erasable read-only memory (EEROM) or other electronic memory; an optical disk or other optical storage; various combinations thereof; or so forth. In some embodiments the non-transitory storage medium storing the instructions is disposed in the US scanner 14, e.g. in the form of an internal hard drive, SSD, flash memory, and/or the like.

In some embodiments, the at least one electronic processor 20 is programmed to apply a trained neural network (NN) 30 to determine tumor contours. For example, the electronic processer can be a Graphical Processing Unit (GPU) for real-time performance during prediction of the tumor contours. The at least one electronic processor may be programmed to perform initial training of the NN 30 using historical neurosurgery patient US images and manually drawn contours serving as ground truth. Alternatively, the initial training may be performed offline, e.g. by a vendor of the US scanner 14 or by a vendor of a neurosurgical image guidance package or add-on for the US scanner 14, and the trained NN 30 is supplied from the vendor and stored on the non-transitory storage medium 28. In either case, patient-specific tuning of the trained NN 30 is preferably performed by the at least one electronic processor 20 as this tuning is performed for each patient and cannot be supplied as a pre-trained component. As the training and patient-specific tuning of the NN 30 is computationally intensive, it is contemplated for the at least one electronic processor 20 to comprise a remote server computer, cloud computing resource, or the like that is operatively connected with the US scanner 14 by a wired or wireless connection (e.g. a wired or wireless connection to a hospital network). In cases where the at least one electronic processor 20 comprises a remote server computer, a vendor may have access to the fine-tuning data at different sites to improve the training and fine-tuning of the NN 30. The NN 30 may also be updated frequently as, for example, a software update. In this configuration, the electronic processor of the US scanner 14 operates the scanner to acquire US images of the patient and to provide the GUI via which a user contours select US images of the patient, and this patient-specific training data is then uploaded to the remote server which performs the patient-specific tuning by update-training the NN 30 using the supplied patient-specific training data. In some illustrative examples, the NN 30 can be a recurrent NN (RNN). In some embodiments, an MR device 32 can be disposed in a medical environment with the US probe 12 and the US scanner 14 to provide additional update training data in the form of contours drawn in update MR images. For example, the NN 30 can be fine-tuned by retraining the NN several times during a procedure with MRI images. A user can the remotely perform the fine-tuning of the NN 30 during the procedure.

Figure 2:
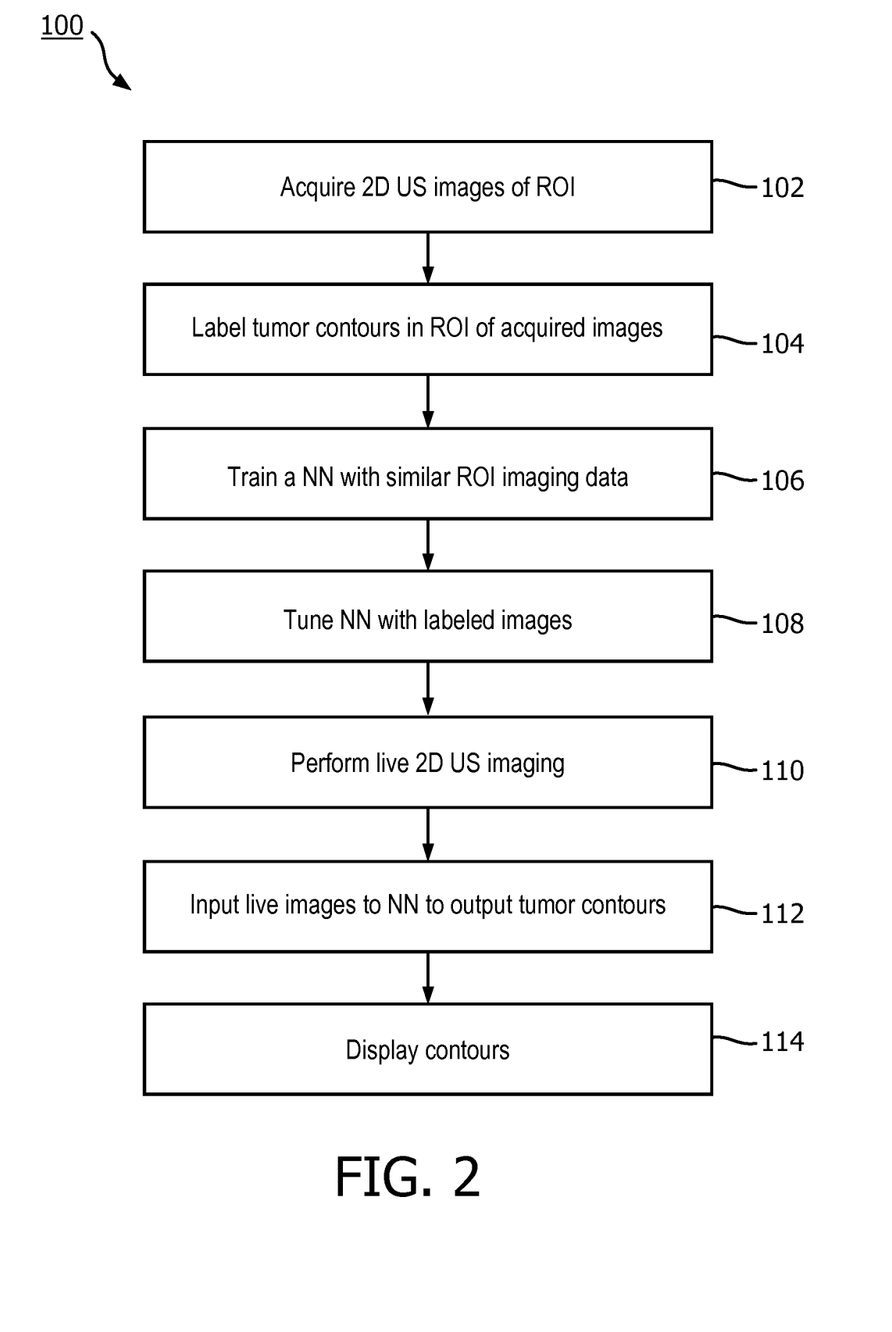
FIG. 2 shows an exemplary flow chart operation of the device of FIG. 1.

With reference to FIG. 2, an illustrative embodiment of the imaging method 100 is diagrammatically shown as a flowchart. To start the process, the US probe 12 is positioned on or near to a portion of the patient to be scanned (e.g., the brain, or more particularly a region of the brain containing the tumor or tumors to be excised). At 102, the at least one electronic processor 20 is programmed to control the US scanner 14 and the US probe 12 to acquire a series of preoperative images (e.g., 2D, 3D, or 4D images) of a tumor and surrounding blood vessels in a region of interest (ROI) of a patient who is about to undergo neurosurgery. In some examples, the ROI can be the brain of the patient. Typically, the operation 102 is performed after the craniotomy but prior to cutting the dura so as to minimize the amount of brain shift in the preoperative US images. In a variant embodiment, the preoperative US imaging operation 102 could be performed before the craniotomy.

At 104, the at least one electronic processor 20 is programmed to provide the GUI 26 via which the acquired preoperative images are labeled with contours of the tumor and the surrounding blood vessels in the ROI. In some examples, the surgeon can use the user input device 22 to label the contours of the tumor on the GUI 26. The GUI 26 can be displayed on the display device 24. The user may delineate a contour, for example, using a mouse or touchscreen to mark points around the contour which are then connected by spline curves or the like, or to draw the entire contour or portions thereof as one or more continuous lines. In other examples, preoperative MR images are acquired with the MR device 32, and contours of the tumor are manually labeled by a medical professional with the user input device 22. At the beginning of the procedure, the probe 12 is registered to the pre-operative MR contours, and the contours are transferred to the acquired US images on the display device 24.

At 106, the at least one electronic processor 20 is programmed to train the NN 30 with US imaging data with MR based tumor contours of similar ROIs of different patients to generate a trained neural network. For example, the imaging data can be retrieved from the non-transitory computer readable medium 28 and applied to the NN 30 to train the NN. It will be appreciated that operation 106 can be performed before, concurrently with, or after operations 102 and/or 104. In offline configurations, e.g. in which a vendor supplies the trained NN 30, the operation 106 is performed before operations 102, 104.

At 108, the at least one electronic processor 20 is programmed to tune the trained NN 30 for the patient using the labeled 2D preoperative images generated in the operations 102, 104 so as to generate a patient-tuned trained neural network. In some embodiments, the at least one electronic processor 20 is programmed to update tune the patient-tuned trained neural network 30 with the labeled 2D live US images (from 104). Additionally, at a later stage of the neurosurgery if the neurosurgeon suspects that the contours superimposed on the live imaging have become out of position due to gradual brain shift, then additional patient-specific training data can be generated by manual contouring of intraoperative images and/or MR images acquired by the in-suite MRI 32 (if available) and the operation 108 repeated with this additional patient-specific data to update the patient-specific tuning of the NN 30.

At 110, the at least one electronic processor 20 is programmed to perform live imaging by controlling the US scanner 14 and the US probe 12 to acquire live (i.e. intraoperative) images (e.g., 2D images) of the tumor and the surrounding blood vessels in the ROI of the patient (e.g., the brain). These images are acquired during the surgical procedure. It should be noted that the live imaging is not necessarily a continuous stream of images. Rather, in some implementations the neurosurgeon may (re-)position the US probe 12 whenever the neurosurgeon desires to have visualization of the tumors so as to acquire new live images.

At 112, the at least one electronic processor 20 is programmed to input the live images to the patient-tuned trained NN to output live contours of the tumor and the surrounding blood vessels. Stated another way, the at least one electronic processor 20 is programmed to apply the NN 30 to the live brain images to generate the live contours of a tumor and surrounding blood vessels imaged in the live brain images. The contours of the tumor and the surrounding blood vessels are thus automatically generated during the surgical procedure. This may be done directly if the US sensor array 16 is capable of sonicating a 3D volume, or may be done in conjunction with a free-hand or motorized sweep of the US probe 12. Preferably, the images are displayed on the display device 24 with the contours output by the operation 112 superimposed (operation 114), so as to provide live US imaging of the interventional procedure with indications (i.e. "live" contours) of the tumor(s) and surrounding blood vessels.

In one embodiment, the at least one electronic processor 20 is programmed to tune the NN 30 using the labeled preoperative images (from 104). In another embodiment, the patient-tuned trained neural network 30 is updated at least partially with contours drawn in intraoperative MR images. To do so, the at least one electronic processor 20 is programmed to control the MR imaging device 32 to acquire an MR image of the ROI during the surgical procedure. The GUI 26 is provided via which the acquired MR image is labeled with contours of the tumor and the surrounding blood vessels (analogous to 104). The US scanner 14 and probe 12 are controlled by the at least one electronic processor 20 to acquire an update series of US images. The GUI 26 is provided or updated by the acquired update series of US images being labeled with contours of the tumor and the surrounding blood vessels. The update series of US images are used to update tune the patient-tuned trained NN 30.

In another embodiment, the acquiring of the live brain images is interrupted, and the at least one electronic processor 20 is programmed to provide the GUI 26 via which selected live brain images are labeled with contours of the tumor and the surrounding blood vessels. The NN 30 is update tuned to generate the live contours using the selected and labeled live brain images.

At 114, the at least one electronic processor 20 is programmed to control the display device 24 to display the live US images with the live contours superimposed. In some examples, the display on the display device 24 includes the live contours superimposed and with reference contours from a spatially registered preoperative magnetic resonance image superimposed. The MRI image can be spatially registered with the US live images, and in some examples, the preoperative MRI image can be displayed in a separate window during surgery so the surgeon can view it.

EXAMPLE

The disclosure includes a machine learning framework using deep learning with convolutional neural networks (CNN) to train on segmented (i.e. contoured) pre-operative MRI, pre-operative US, segmented intra-operative MRI and intra-operative US, to understand how different tumors look like in MRI vs US, what are their similar or dissimilar features. During the training, MRI's provide ground truth by manually performed segmentations, which are overlaid on the US images, which serves as the training data, via tracked acquisition.

Once the network is trained it will be deployed as a software onto workstations used by the surgeons during surgery, alternatively it can be loaded onto an ultrasound scanner, to provide additional information during intraoperative US exam based on the pre-operative MRI and US images.

The data necessary to train a deep neural network for automated tumor identification during neurosurgery consists of registered ultrasound (US) and magnetic resonance (MR) image pairs. The MR images serve as ground truth since most brain lesions are visible in MR images and segmented from MR images. Here all the segmentations are assumed to be performed by an expert in the field, hence the ground truth. The segmentation is represented as a binary volume matrix where inside the tumor volume has a value of one and outside has a value of zero. Corresponding US image data is always acquired while being tracked so a high accuracy registration between US and MR images can be performed. Tracked pre-operative and intra-operative US images (intra-operative US can only be used if there is a matching intra-op segmented MR image to pair it with) are used to create a volume, which will be called as a training sample. For each training sample the training is performed with a corresponding registered segmentation volume. Finally the segmentation information is carried over to the ultrasound image to identify the tumor in the ultrasound image.

Figure 3:
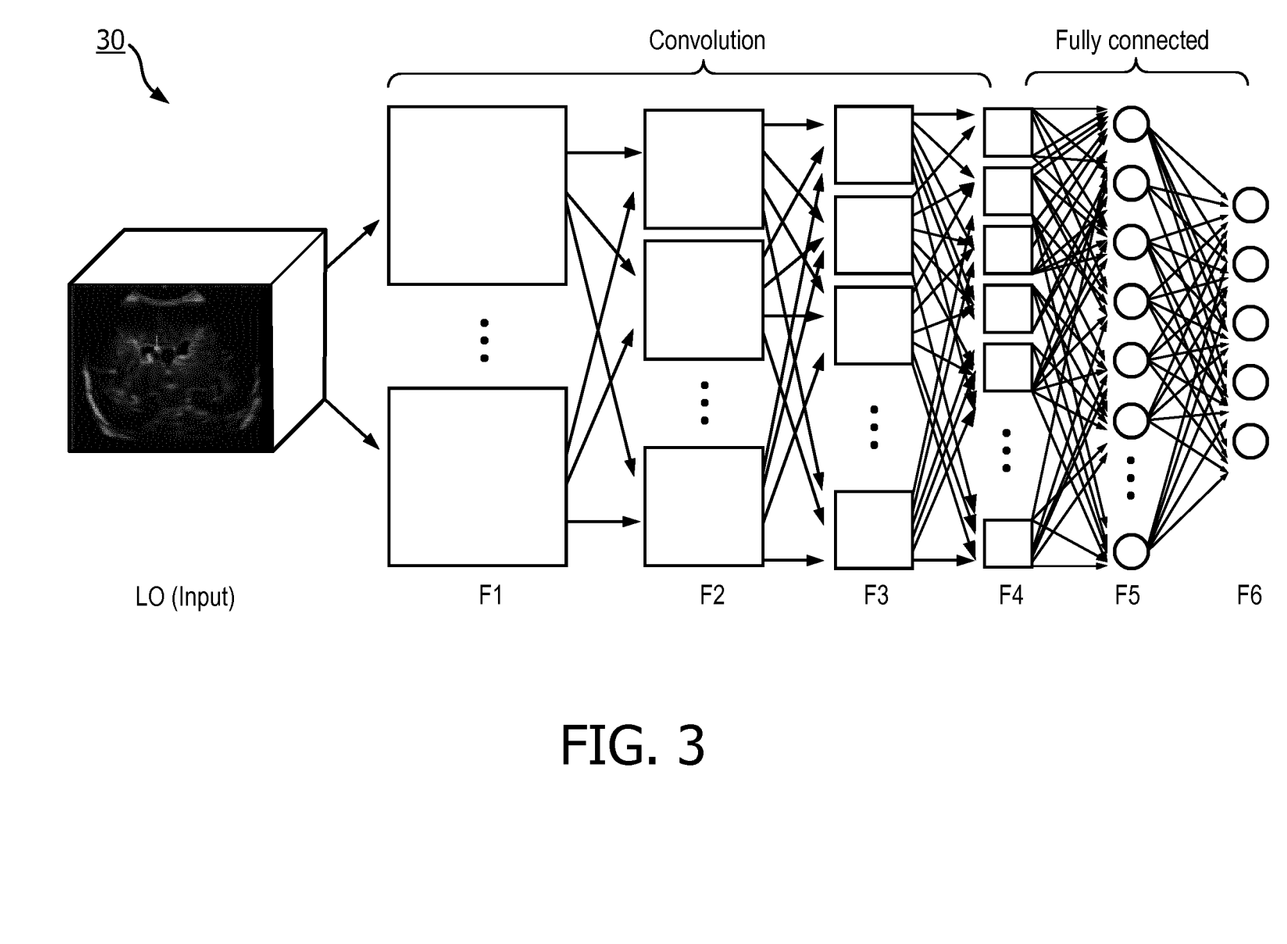
FIG. 3 shows an example schematic of a neural network of the device of FIG. 1.

FIG. 3 shows a schematic of an example convolutional neural network. Input is a volume generated from tracked and registered ultrasound images. Target values are binary segmentation maps of the same geometry manually obtained from MR images. The objective of the convolutional neural network is to determine the residual tumor segmentation from ultrasound images, therefore a network architecture with US images as the input is proposed. In order to train this network, target (ground truth outputs used during training) segmentation results obtained by processing the MR images, overlaid on the input ultrasound images are used. Such an architecture uses several convolutional layers in the first layers coupled with pooling layers. Typically convolutional layers are followed by one or more fully connected layers and finally by the output layer which returns the probability values for the pixel values of the binary segmentation map.

The network is trained using standard neural network training techniques such as backpropagation for a large enough training data. There can be significant inter-patient variation in tumor appearance and output of the model after the initial population based training may not be accurate enough for each case. In order to address this, the network is fine-tuned using the pre-operative MR and US images acquired after the craniotomy, on the day of surgery. This patient specific fine tuning step is an essential part of the workflow and will help the model to adopt to the specific case which it will be used during surgery. The neurosurgeon can perform an ultrasound sweep without disrupting the workflow in any point during the surgery. The resulting tracked and registered US volumes are sent to the neural network to make predictions of the residual tumor in the swept volume. The predicted segmentation map indicating the tumor areas can either be displayed as a contour for boundary of the binary segmentation map or in pseudo-color overlaid on top of the image indicating the probabilities of the tumor regions.

Figure 4:
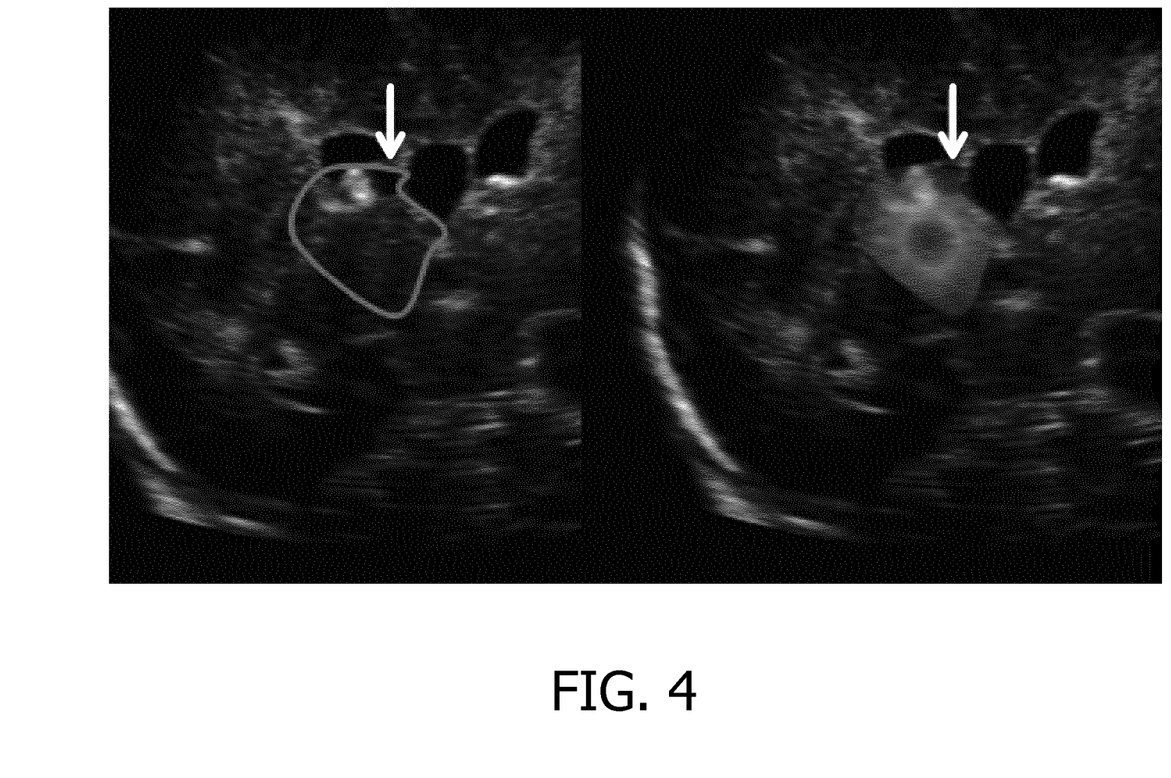
FIG. 4 shows images with contours generated by the device of FIG. 1.

These two display formats are shown in FIG. 4. FIG. 4 shows a contour predicating the tumor site on the "left" side of the image, and the "right" side shows a heat-map displaying the probability of a tumor, where the color-shading darkens as the likelihood of the tumor location increases.

Alternatively a tracked intraoperative US sweep can be performed and all the output images are used to construct a new, updated registered volume, where remaining tumor locations are marked using the neural network predictions. This recently acquired volume and its predicted segmentation is then used to display remaining tumor relative to the tracked resection or other interventional tool.

In an alternative embodiment, it is possible to further fine tune the trained network using a reinforcement learning framework, if intra-operative MR is present during the surgery. The trained network can still be used to make predictions from the intra-operative ultrasound volumes, these are then compared with the segmentations from the intra-op MR. The model can be penalized for erroneously estimating non-tumor tissue as tumor or vice-versa. This helps the model to adapt to the current case and make more accurate future predictions of the current case.

The trained neural network is embedded in a software to make predictions during surgery. This software can run on the ultrasound scanner to estimate the residual tumor segmentation in real time as the images are being acquired.

The disclosure has been described with reference to the preferred embodiments. Modifications and alterations may occur to others upon reading and understanding the preceding detailed description. It is intended that the disclosure be construed as including all such modifications and alterations insofar as they come within the scope of the appended claims or the equivalents thereof.

The invention claimed is:

1. An ultrasound (US) system, comprising:
a US scanner and a US probe operatively connected to the US scanner; and
at least one electronic processor programmed to:
control the US scanner and US probe to acquire a series of preoperative US images of a tumor and surrounding blood vessels in a region of interest (ROI) of a patient;
provide a graphical user interface (GUI) which displays the preoperative US images of the tumor and the surrounding blood vessels in the ROI of the patient and via which the preoperative US images of the tumor and the surrounding blood vessels in the ROI of the patient are manually labeled with contours of the tumor and the surrounding blood vessels in the ROI;
tune a trained neural network (NN) for the patient using only the labeled preoperative US images of the tumor and the surrounding blood vessels in the ROI of the patient to generate a patient-tuned trained neural network;
perform, during a surgical procedure, live imaging of the tumor and the surrounding blood vessels in the ROI of the patient of which the preoperative US images of the tumor and the surrounding blood vessels are taken by controlling the US scanner and US probe to acquire live US images of the tumor and the surrounding blood vessels in the ROI of the patient;
input the live US images of the tumor and the surrounding blood vessels in the ROI of the patient to the patient-tuned trained NN to output live contours of the tumor and the surrounding blood vessels; and
control a display device to display the live US images of the tumor and the surrounding blood vessels in the ROI of the patient with the live contours superimposed.

2. The system of claim 1, wherein the at least one electronic processor is further programmed to:
control the display device to display the live US images with the live contours superimposed and with contours from a spatially registered preoperative magnetic resonance image superimposed.

3. The system of claim 1, wherein the at least one electronic processor is further programmed to:
prior to the tuning, train a NN with imaging data of similar ROIs of different patients to generate the trained neural network.

4. The system of claim 3, wherein the at least one electronic processor is further programmed to:
provide the GUI via which a selected one or more of the live US images of the tumor and the surrounding blood vessels in the ROI of the patient are manually labeled with contours of the tumor and the surrounding blood vessels in the ROI; and
update tune the patient-tuned trained NN with the labeled live US images.

5. The system of claim 3, wherein the at least one electronic processor is further programmed to:
control an MR imaging device to acquire an MR image of the ROI;
provide the GUI via which the acquired MR image is manually labeled with contours of the tumor and the surrounding blood vessels;
control the US scanner and the US probe to acquire an update series of US images;
provide the GUI via which the acquired update series of US images are manually labeled with contours of the tumor and the surrounding blood vessels; and
update tune the patient-tuned trained neural network with the update series of US images.

6. The system of claim 1, wherein the NN is a recurrent NN (RNN).

7. The system of claim 1, wherein the region of interest is a brain.

8. A live brain imaging method, the method comprising:
after performing a craniotomy on a patient but prior to cutting a dura of the patient, controlling an ultrasound (US) system to acquire 2D preoperative brain images of the patient;
providing a graphical user interface (GUI) on a display via which the 2D preoperative brain images of the patient acquired after the craniotomy but prior to cutting the dura are manually labeled with contours of a tumor and surrounding blood vessels imaged in the preoperative brain images of the patient;
tuning a trained neural network (NN) for the patient using the labeled preoperative brain images of the patient acquired after the craniotomy but prior to cutting the dura to generate a patient-tuned trained NN;
during brain surgery performed on the patient after the cutting of the dura, controlling the US system to acquire two dimensional (2D) live brain images of the patient;
applying the patient-tuned trained NN to the 2D live brain images of the patient acquired during the brain surgery performed on the patient after the cutting of the dura to generate live contours of the tumor and the surrounding blood vessels imaged in the 2D live brain images of the patient; and
during the brain surgery performed on the patient after the cutting of the dura, controlling the display device to present the 2D live brain images of the patient with the live contours superimposed.

9. The live brain imaging method of claim 8, further comprising:
interrupting the acquiring of the live brain images and providing the GUI via which selected live brain images are manually labeled with contours of the tumor and the surrounding blood vessels; and update tuning the neural network used to generate the live contours using the selected and labeled live brain images.

10. The live brain imaging method of claim 8, further comprising:
   prior to controlling the US system to acquire the 2D live brain images, training the neural network used to generate the live contours using labeled ultrasound brain images of previous patients which are labeled with contours of the tumor and surrounding blood vessels.

11. The live brain imaging method of claim 8, wherein the controlling of the display device comprises:
   controlling the display device to present the 2D live brain images with the live contours superimposed and also with superimposed reference contours obtained from a preoperative magnetic resonance image that is spatially registered with the 2D live brain images.

12. An ultrasound (US) system, comprising:
   a US scanner and a US probe operatively connected to the US scanner; and
   at least one electronic processor programmed to:
   control the US scanner and the US probe to acquire two dimensional (2D) live images of a region of interest (ROI);
   apply a neural network to the 2D live brain images to generate live contours of a tumor and surrounding blood vessels imaged in the 2D live images;
   control a display device to present the 2D live images with the live contours superimposed;
   interrupt the acquiring of the live images and provide a graphical user interface (GUI) via which selected live images are manually labeled with contours of the tumor and the surrounding blood vessels;
   update tune the neural network used to generate the live contours using the selected and labeled live images.

13. The system of claim 12, wherein the at least one electronic processor is further programmed to:
   prior to acquiring the 2D live images, control the US scanner and the US probe to acquire a series of 2D preoperative images;
   provide a graphical user interface (GUI) via which the 2D preoperative brain images are manually labeled with contours of the tumor and the surrounding blood vessels; and
   tune the neural network used to generate the live contours using the labeled 2D preoperative images.

14. The system of claim 12, wherein the at least one electronic processor is further programmed to:
   prior to controlling the US scanner and the US probe to acquire the 2D live images, train the neural network used to generate the live contours using labeled ultrasound images of previous patients which are labeled with contours of the tumor and surrounding blood vessels.

15. The system of claim 12, wherein the at least one electronic processor is further programmed to:
   control the display device to present the 2D live images with the live contours superimposed and also with superimposed reference contours obtained from a preoperative magnetic resonance image that is spatially registered with the 2D live images.

16. The system of claim 14, wherein the at least one electronic processor is further programmed to:
   control an MR imaging device to acquire an MR image of the ROI;
   provide the GUI via which the acquired MR image is manually labeled with contours of the tumor and the surrounding blood vessels;
   control the US scanner and the US probe to acquire an update series of 2D US images;
   provide the GUI via which the acquired update series of US images are manually labeled with contours of the tumor and the surrounding blood vessels; and
   update tune the patient-tuned trained neural network with the update series of 2D US images.

17. The system of claim 12, wherein the NN is a recurrent NN (RNN).

18. The system of claim 12, wherein the region of interest is a brain.

* * * * *